(12) United States Patent
Singh et al.

(10) Patent No.: US 7,462,708 B2
(45) Date of Patent: Dec. 9, 2008

(54) **TEMPERATURE REGULATED PROMOTERS FROM *SCHIZOSACCHAROMYCES POMBE* FOR EXPRESSION OF PROTEINS**

(75) Inventors: Jagmohan Singh, Chandigarh (IN); Raj Kumar, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 450 days.

(21) Appl. No.: 10/813,156

(22) Filed: Mar. 31, 2004

(65) Prior Publication Data

US 2005/0221425 A1   Oct. 6, 2005

(51) Int. Cl.
*C12N 15/11*   (2006.01)
*C12N 15/09*   (2006.01)
*C12N 15/22*   (2006.01)
*C12N 15/00*   (2006.01)
*C12N 15/81*   (2006.01)

(52) U.S. Cl. .................. 536/24.1; 536/23.1; 435/320.1; 435/69.1; 435/483; 435/254.21

(58) Field of Classification Search ....................... None
See application file for complete search history.

(56) References Cited

FOREIGN PATENT DOCUMENTS

WO      WO 94/03609      *   2/1994

OTHER PUBLICATIONS

Forsburg, S.L., The Forsburg Lab pombe Pages: Working with fission yeast, downloaded from the web Feb. 12, 2008.*

* cited by examiner

*Primary Examiner*—Maria Marvich
(74) *Attorney, Agent, or Firm*—Sughrue Mion, PLLC

(57) ABSTRACT

The present invention relates to novel temperature promoters and set of expression vectors isolated from *Schizosaccharomyces pombe*. The vectors so developed can be used for regulated expression of proteins, both homologous and heterologous, very efficiently and economically.

12 Claims, 12 Drawing Sheets

*nmt1* promoter

Figure 2:
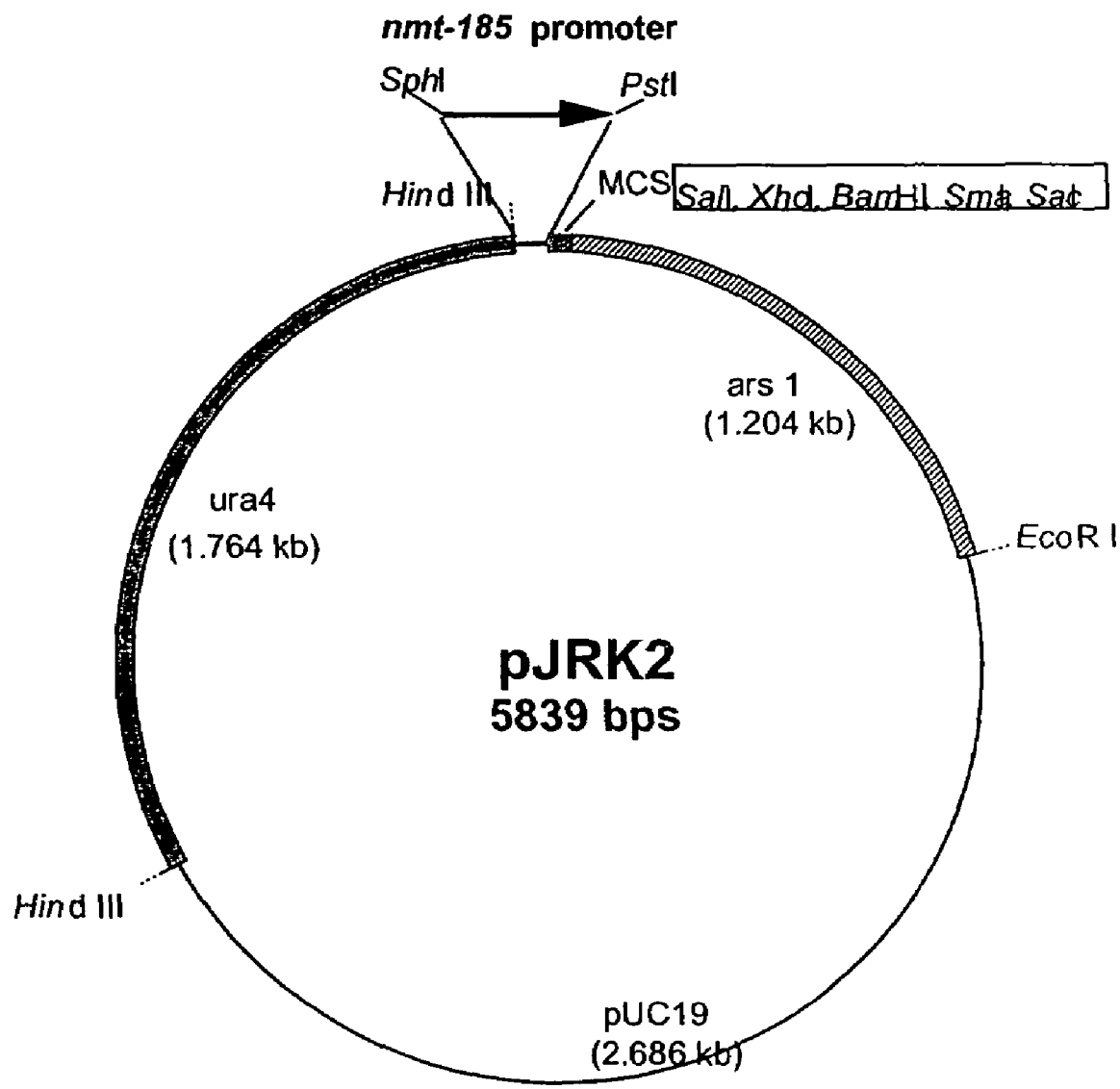

```
-1178 TGATCAGAA AATTATCGCC ATAAAAGACA GAATAAGTCA TCAGCGGTTG  TTTCATTTCC TA
-1116 TATTTTTTTT TTATTTTTTT ATTTTTTAAT AAGGGAAAAT TTAACGTCTA  AGGATACAGA AG
-1054 ATTGTTAGCA CATTAAAGTA ATAAAGGCTT AAGTAGTAAG TGCCTTAGCA  TGTTATTGTA TT
-992  TCAAAGGACA TAATCTAAAA TAATAACAAT ATCATTTCTC ACAAGTTATT  CAATTTTCTT TT
-930  TTTTTTCTAA TAATATCAAG AATGTATTAT TTGTTTGACA TAAGTCAACT  AATTTATTTA AT
-868  ATGCTGGATT AATCTTGCAG ACATGTAAAT TAACAAGTTT TAGTCAAATA  ACGTTGAAGT TT
-806  CAATGAACTC AAATAATTTC TCTTTTTTTT TATATAACCA TATGTCTAAT  CTGATTTATA TT
-744  TTCCGCAGGA TCAACTGAAG TTATGACATT TGGATTGGAT CACTTATAAC  CTTGGTCGCC AA
-682  ATAATACAAA AATCAGCGTT ATAAAACAAA GAAGGTTTTT GTTAAGAAAT  TAATCCTCTT TC
-620  TTGATAAGAA AGTTGAACCG AAATTGCAGA TACTGATATA TGAAAATAAT  ACCCACAATT TT
-558  GGGAATAGCG CAAGCCTCAA TTTAAACAAT AGGTGAGGAC ACATGATAAT  GACCTCAATG AT
-496  TGTTAGAAGA AAAGAGCCTC ATTACAAAAT CGAAAAATGA ATGGTTGGGT  ACAAGTTTCC AA
-434  AACATGGTAA AGTGGACTTT GCGTATGAGA CGTAAATAGA AAAAAACACT  TGTTATATGT TT
-372  TCTAGAATTA TTGTTGTCTC TTTATGGTTG GATGATGCAA AATAGTAATT  TCGGTTAGTT GC
-310  TGTAAAACAC CACGAGACAA ATAGATATGG ATATTTATTA AATCAGGAAA  AACGTAACTC TC
-248  GGCTACTGGA TGGTTCAGTC ACCCAACGAT TACTGGGGAG AGAAAACAGG  GCAAAAGCAA AG
-186  CTTAAAGGAA TCCGATTGTC ATTCGGCAAT GTGCAGCGAA ACTAAAAACC  GGATAATGGACC
-124  TGTTAATCGA AACATTGAAGA TATATAAAG GAAGAGGAAT CCTGGCATAT  CATCAATTGA AT
-62   AAGTTGAATT AATTATTTCA ATCTCATTCT CACTTTCTGA CTTATAGTCG  CTTTGTTAAA TC
 1    ATGTCTACTA ACAAGATCAC TT
```

SEQ ID No.1 : *nmt-185* promoter
AAAGGAATCCGATTGTCATTCGGCAATGTGCAGCGAAACTAAAAACCGGATAATGGACC
TGTTAATCGAAACATTGAAGATATATAAAGGAAGAGGAATCCTGGCATATCATCAATTGA
ATAAGTTGAATTAATTATTTCAATCTCATTCTCACTTTCTGACTTATAGTCGCTTTGTTAA
ATCAT SEQ ID No.2 : *nmt-146* promoter
TAAAAACCGGATAATGGACCTGTTAATCGAAACATTGAAGATATATAAAGGAAGAGGAATCCTG
GCATATCATCAATTGAATAAGTTGAATTAATTATTTCAATCTCATTCTCACTTTCTGACTTATAGTC
GCTTTGTTAAATCAT

Figure 1.

A 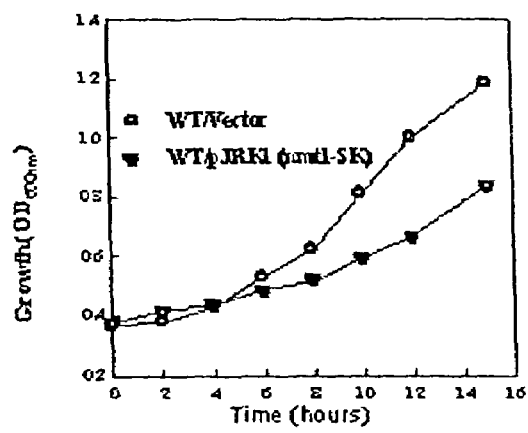  B 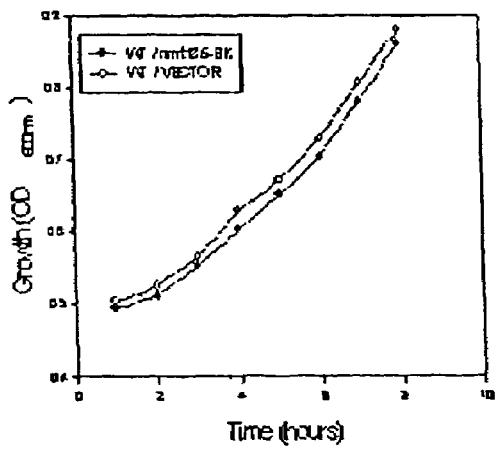
FIGURE 11

SEQUENCE LISTING

```
<160> NUMBER OF SEQ ID NOS: 3

<210> SEQ ID NO 1
<211> LENGTH: 1199
<212> TYPE: DNA
<213> ORGANISM: Schizosaccharomyces pombe

<400> SEQUENCE: 1
tgatcagaaa attatcgcca taaaagacag aataagtcat cagcggttgt ttcatttcct      60
atattttttt tttattttttt tatttttttaa taagggaaaa tttaacgtct aaggatacag     120
aagattgtta gcacattaaa gtaataaagg cttaagtagt aagtgcctta gcatgttatt     180
gtatttcaaa ggacataatc taaaataata acaatatcat ttctcacaag ttattcaatt     240 ttctttttttt tttctaataa tatcaagaat gtattatttg tttgacataa gtcaactaat     300
ttatttaata tgctggatta atcttgcaga catgtaaatt aacaagtttt agtcaaataa     360
cgttgaagtt tcaatgaact caaataattt ctctttttttt ttatataacc atatgtctaa     420
tctgatttat attttccgca ggatcaactg aagttatgac atttggattg gatcacttat     480
aaccttggtc gccaaataat acaaaaatca gcgttataaa acaagaagg tttttgttaa     540 gaaattaatc ctctttcttg ataagaaagt tgaaccgaaa ttgcagatac tgatatatga     600
aaataatacc cacaatttttg ggaatagcgc aagcctcaat ttaaacaata ggtgaggaca     660
catgataatg acctcaatga ttgttagaag aaaagagcct cattacaaaa tcgaaaaatg     720
aatggttggg tacaagtttc caaaacatgg taaagtggac tttgcgtatg agacgtaaat     780
agaaaaaaac acttgttata tgttttctag aattattgtt gtctctttat ggttggatga     840
tgcaaaatag taatttcggt tagttgctgt aaaacaccac gagacaaata gatatggata     900
tttattaaat caggaaaaac gtaactctcg gctactggat ggttcagtca cccaacgatt     960
actggggaga gaaacaggg caaaagcaaa gcttaaagga atccgattgt cattcggcaa     1020
tgtgcagcga aactaaaaac cggataatgg acctgttaat cgaaacattg aagatatata     1080
```

```
aaggaagagg aatcctggca tatcatcaat tgaataagtt gaattaatta tttcaatctc    1140
attctcactt tctgacttat agtcgctttg ttaaatcatg tctactaaca agatcactt     1199

<210> SEQ ID NO 2
<211> LENGTH: 185
<212> TYPE: DNA
<213> ORGANISM: Schizosaccharomyces pombe

<400> SEQUENCE: 2
aaaggaatcc gattgtcatt cggcaatgtg cagcgaaact aaaaaccgga taatggacct      60
gttaatcgaa acattgaaga tatataaagg aagaggaatc ctggcatatc atcaattgaa     120
taagttgaat taattatttc aatctcattc tcactttctg acttatagtc gctttgttaa     180
atcat                                                                185

<210> SEQ ID NO 3
<211> LENGTH: 146
<212> TYPE: DNA
<213> ORGANISM: Schizosaccharomyces pombe

<400> SEQUENCE: 3
taaaaaccgg ataatggacc tgttaatcga acattgaag atatataaag gaagaggaat       60
cctggcatat catcaattga ataagttgaa ttaattattt caatctcatt ctcactttct     120
gacttatagt cgctttgtta aatcat                                         146
```

TEMPERATURE REGULATED PROMOTERS FROM *SCHIZOSACCHAROMYCES POMBE* FOR EXPRESSION OF PROTEINS

FIELD OF INVENTION

The present invention relates to novel temperature promoters and set of expression vectors isolated from *Schizosaccharomyces pombe*. The vectors so developed can be used for regulated expression of proteins, both homologous and heterologous, very efficiently and economically.

BACKGROUND INFORMATION

Early search for new promoters in *S. pombe* yielded adh1, a strong but constitutive promoter, which drives the expression of the glycolytic enzyme alcohol dehydrogenase. This promoter has been used in the vectors pART1 and pEVP11 (Russell, 1989, In: Molecular Biology of the Fission Yeast. San Diego: Academic Press, Inc. Nasim. A., Young, P., and Johnson, B. F., Eds. pp. 243-71). Among the inducible promoters are the glucose regulated promoter fructose bisphosphase (fbp) (Hoffman and Winston, 1989, Gene 84: 473-79) and the invertase promoter (inyl) (Tanaka et al., 1998, Biochem. Biophys. Res. Commun. 245: 246-53), which have been used successfully to express a number of proteins including GFP. The strongest known promoter in *S. pombe* is adh1, which is a constitutively expressed promoter. Although expression driven by this promoter can yield levels of protein to the extent of 0.5-2% of total cellular protein (Russell, 1989, In Molecular Biology of the Fission Yeast. San Diego: Academic Press, Inc. Nasim. A., Young, P., and Johnson, B. F., Eds. pp. 243-271), it can pose difficulties when the expression of toxic proteins is desired. Therefore, researchers have always focused their attention to the development of inducible promoters.

The regulatable promoters in *S. pombe* include the fbp, inv1 and nmt1. The fbp1 promoter is repressed by 8% glucose and derepressed in 0.1% glucose plus 3% maltose (Hoffman and Winston, 1989, Gene 84: 473-479). A limitation of this promoter is that it is derepressed in stationary phase and furthermore, the cells expressing the vector do not grow well under the inducing conditions. A similar drawback is faced by the inv1 promoter derived from the inv1gene that codes for invertase in *S. pombe* (Tanaka et al., 1998, Biochem. Biophys. Res. Commun. 245: 246-53). It is also repressed by glucose and derepressed by depletion of glucose. The regulation of expression using this promoter cannot be very tight because of progressive depletion of glucose in the culture medium as a result of its utilization during the cellular growth. Likewise another inducible promoter of *S. pombe* be acid phosphatase structural gene (pho1), which is induced by low concentrations of inorganic phosphate in the medium, has the drawback that it shows a significant level of uninduced transcription, thus negating its potential use as a promoter (Maundrell, 1990, J. Biol. Chem. 265: 10857-64). Thus, to date only one promoter element has come to be used regularly as a research tool, namely nmt1, which is repressed by high concentration of thiamin and induced by absence of thiamin (Maundrell, 1990, J. Biol. Chem. 265: 10857-64). The most common and the strongest form of this promoter is nmt1. A few derivatives of the nmt1 promoter were subsequently developed that yield very high (nmt1), medium (nmt41) and low (nmt81) levels of expression (Forsburg, 1993, Nucleic Acid Res. 21: 2955-56). A related problem of these promoters is their leakiness even under repressed conditions and the leakiness appears to be directly proportional to the promoter strength (Forsburg, 1993, Nucleic Acid Res. 21: 2955-2956). The induction regime involves growth of cells harboring the plasmid expressing a particular gene under the control of the nmt1 promoter in presence of thiamin. After growing to early log phase ($OD_{600}$ of ~0.3), cells are washed with and transferred to a synthetic medium lacking thiamin and grown further. The expression of the gene of interest is observed after nearly 18-20 hours of growth in the medium lacking thiamin. Apart from the cumbersome problem of handling cells under sterile conditions through the steps of washing and resuspension in thiamin-free medium, the other major problem with this promoter is that it is leaky, that is, the expression of the gene is never completely repressed in the presence of thiamin. This can lead to a deleterious effect on the growth rate of cells even before the start of induction because of possible metabolic load. A similar effect may be exerted during induction because of the long time of induction to achieve full expression level. The presence of the heterologous protein during the long induction period in the intracellular milieu may also lead to cellular defect and protein degradation. The present invention therefore obviates these drawbacks and through the process of this invention a temperature sensitive (or regulated) promoter based vector for expression of heterologous proteins in fission yeast, *Schizosaccharomyces pombe* has been developed. This invention is particularly useful in efficient, economic and regulated expression of proteins both homologous and heterologous.

The new promoter elements are isolated by screening of promoters which allow expression of a Green fluorescent protein (GFP) reporter gene in response to a shift in temperature. The promoter elements thus isolated represent a truncated region of the previously reported no-message for thiamine 1 (nmt1) promoter (Maundrell, 1990, J. Biol. Chem. 265: 10857-64) having some unique properties that make them more advantageous to use as compared to other known promoters including nmt1 in *Schizosaccharomyces pombe* (*S. pombe*).

These characteristics are: i) temperature sensitive expression: induction of expression by shifting the temperature from 36° C. to 25° C., ii) faster kinetics of expression, iii) moderate level of expression, iv) low leaky expression and v) lack of toxicity.

Selection of a suitable promoter is the most important factor in obtaining optimum level of expression. In early studies, several promoters that work in *Saccharromyces cerevisiae* (*S. cerevisiae*) were tried in *S. pombe*, but with limited success. The promoters that provided a good level of expression included phosphoglycerate kinase (PGK), alcohol dehydrogenase I (ADH1) and iso-1-cytochrome c (CYC). Among other heterologous promoters that work in *S. pombe* are the simian virus (SV40) promoter, human cytomegalovirus (hCMV) promoter, cauliflower mosaic virus (CaMV) 35S promoter, tomato nitrate reductase promoter, human serum albumin TATA element, adenovirus region 3 promoter, human immunodeficiency virus-1 Long terminal repeat (HIV-1 LTR) promoter etc. Another expression system combines the CaMV promoter and tetracycline regulatory sequences to elicit tetracycline regulated expression. Recently, a co-transformation strategy using a vector containing the hCMV promoter and another vector containing the autonomous replication sequence (ars1) and stable (stb) elements has been reported {review by Giga-Hama, 1997, in Foreign Gene Expression in Fission Yeast *Schizosaccharomyces pombe* (Giga-Hamma and Kumagai, Eds.), Springer-Verlag, Berlin pp. 3-28}.

The advantages of the new promoters vis-a-vis the nmt1 and its other known derivative promoters strongly support the aspects of novelty and lack of obviousness and anticipation. In fact, literature published on the characteristics of the nmt1 promoters have only focussed on the minimal size of the nmt1 promoters that is repressible by thiamin and on the role of trans-acting factors. No investigation has envisaged or anticipated in published literature whether derivatives of the nmt1 promoter having altogether new characteristics different from the original parent promoter could be derived. In fact, from our screen we were expecting to isolate heat-inducible promoters, like heat shock promoters, rather than the temperature sensitive ones that we actually obtained. Thus, identification of promoter that is heat sensitive, was an unexpected discovery for us as well. Therefore, we believe that these points will strengthen the claims for lack of obviousness and anticipation in obtaining the present set of promoters.

OBJECTS OF THE INVENTION

The main objective of the present invention, therefore, is to develop expression vectors based on novel promoter elements isolated from *Schizosaccharomyces pombe*.

Another objective of the invention is to develop vectors with regulatable promoters, which are regulated by temperature shift.

Yet another objective of the invention is to use these vectors as substitutes for the nmt1 promoter based vector.

Yet another objective of this invention is to develop promoters with faster kinetics of induction of expression.

Yet another objective of this invention is to develop alternative, simpler, cheaper and user-friendly modes of induction that are easier to perform as compared to nmt1.

Yet another objective of this invention is to develop expression systems in which heterologous protein expression does not affect the viability of the host cells.

Therefore the present invention relates to expression vectors based on novel regulatable promoter elements isolated from *Schizosaccharomyces pombe* which comprise:
(i) Construction of a fission yeast promoter library wherein a partial Sau3AI library of genomic DNA was cloned upstream of the GFP reporter gene, using known procedures,
(ii) Screening of *S. pombe* promoter library using known procedure wherein cells plated on to suitable plates were examined under reflected UV light to monitor expression of the GFP reporter gene under different conditions of growth,
(iii) Isolating from the genomic library as constructed in step (i), two clones having genomic DNA fragment of *S. pombe*, allowing GFP expression,
(iv) using the said clones to regulate the GFP expression by temperature shift,
(v) Sequencing the genomic DNA fragments as obtained in the step (iii) above as novel promoter elements which were 185 and 146 bases long,
(vi) Construction of new vectors pJRK2 and pJRK3 by cloning the promoter elements as obtained in step (v) above, respectively. These two vectors have been deposited in International Depository Authority on Microbial Type Culture Collection and have been given accession nos. MTCC 5106 and MTCC 5107, respectively,
(vii) Characterization of the promoter elements as nmt-185 and nmt-146,
(viii) Determining the strength of new promoters using GFP and β-galactosidase as reporter genes, and
(xi) Using the promoters to express other genes like streptokinase and cdc18.

BRIEF DESCRIPTION OF THE ACCOMPANYING DRAWINGS/FIGURES

FIG. 1 DNA sequences of nmt 1(SEQ ID NO: 3), nmt-185 (SEQ ID NO: 1), and nmt-146 (SEQ ID NO: 2), promoter. In the sequence of nmt 1 promoter, the horizontal arrow indicated the site of transcription initiation and this site occurs 27 base pairs downstream of the sequence TATATAAA in the red background.

FIG. 2 New vector having Accession No. MTCC 5106 harbouring nmt-185 promoter.

Figure 3:
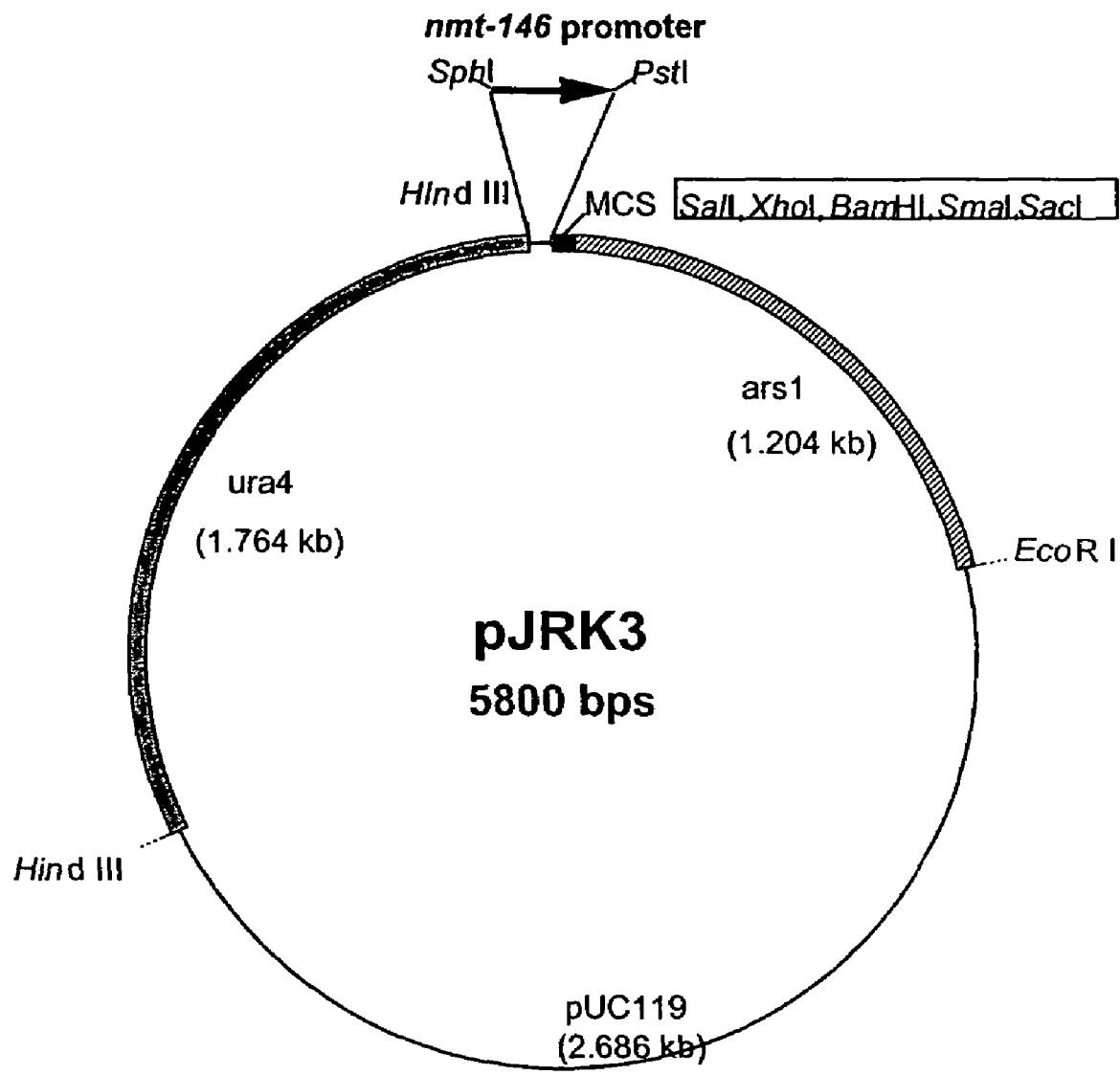

FIG. 3 New vector having Accession No. MTCC 5106 harbouring nmt-146 promoter

Figure 4:
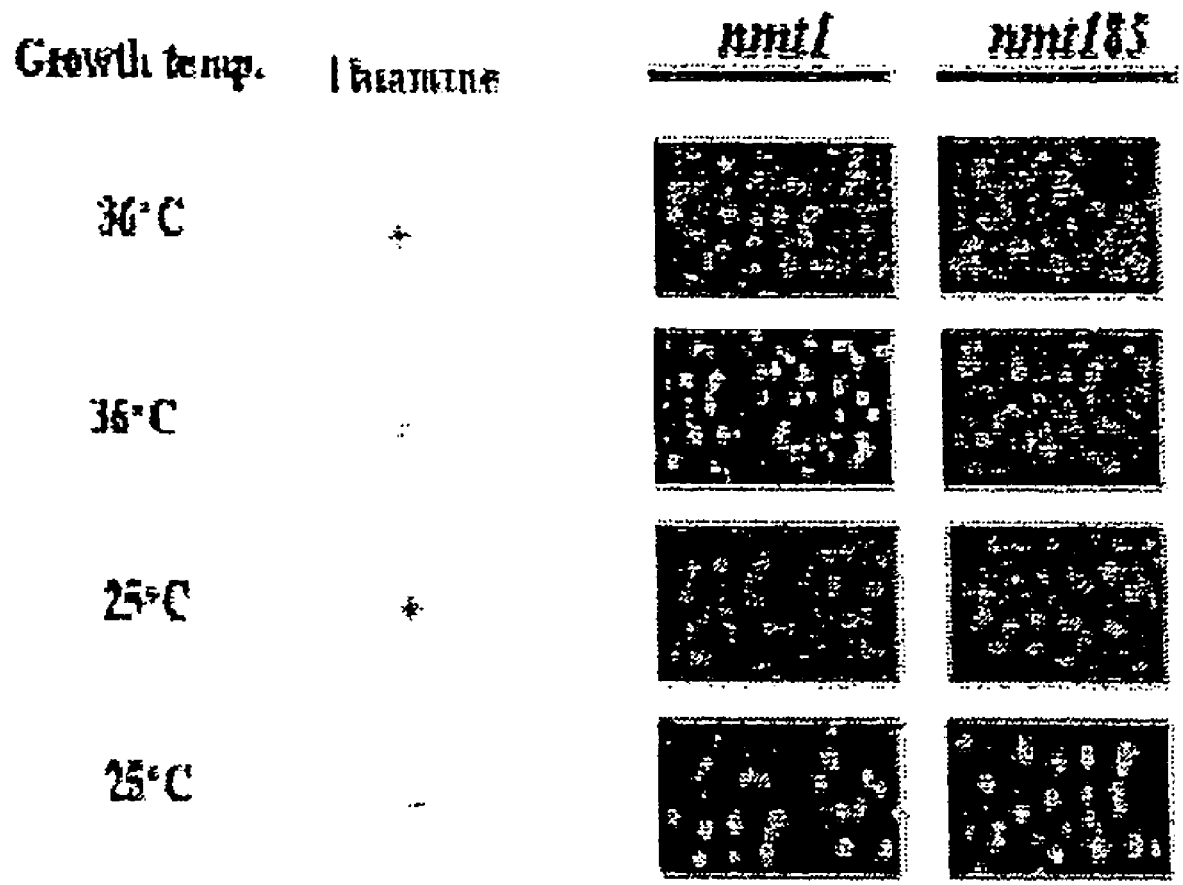

FIG. 4 GFP expression under the control nmt1 and nmt-185 promoters

Wild type *S. pombe* strains expressing GFP gene under the control of the nmt1 or nmt-185 promoters were streaked on PMA-leu plate in presence and absence of thiamine at 37° C. or 25° C. After 2 days of incubation, photograph was taken under reflected UV light.

Figure 5:
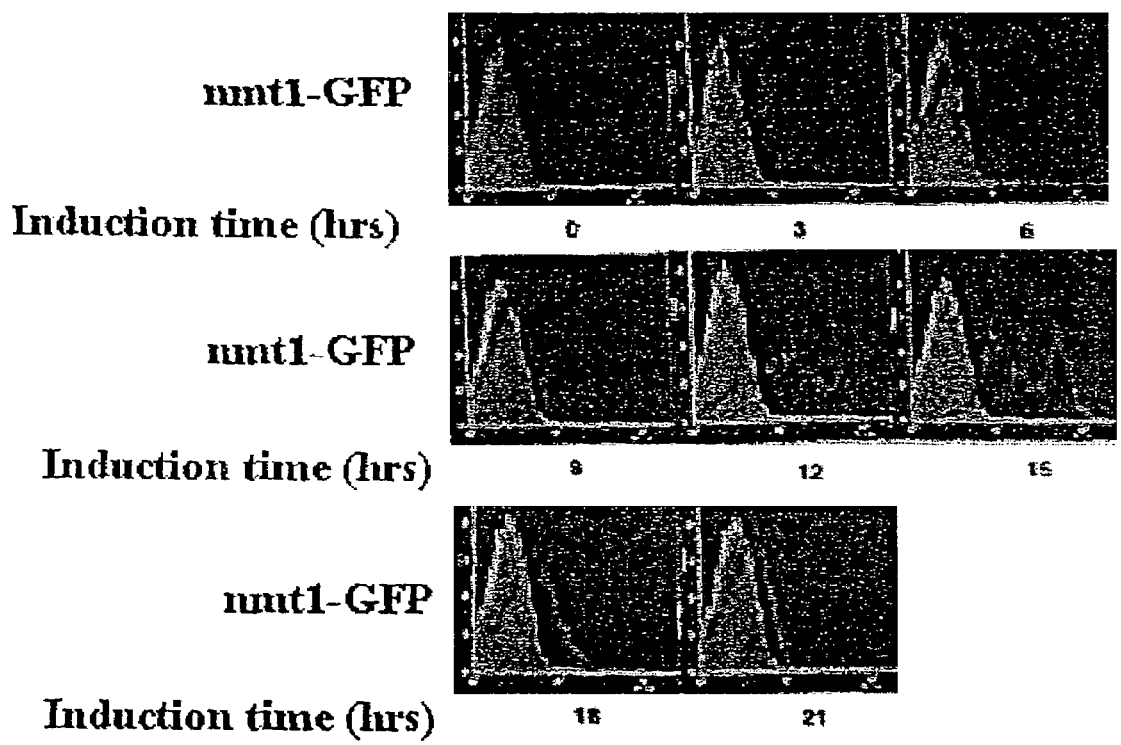

FIG. 5 GFP expression under the control of nmt1 promoter was monitored at cellular level by FACS analysis The wild type strain of *S. pombe* harbouring the plasmid expressing GFP gene under the control of nmt1 promoter was grown up to mid-log phase at 37° C. in presence of thiamine (promoter off) and then transferred to fresh medium lacking thiamine and further grown at 25° C. Samples were taken at 0, 3, 6, 9, 12, 15, 18 and 21 hrs of induction and analyzed. 10,000 cells were analysed for fluorescence intensity using a Becton Dickson FACsort flow cytometer. Excitation was at 488 nm and detection was through a 530-30 nm filter. Counts: number of cells showing a given fluorescence. FL1-H: Fluorescence filter 1. For comparison, the background autofluorescence of the wild type strain is superimposed on the same profile.

Figure 6:
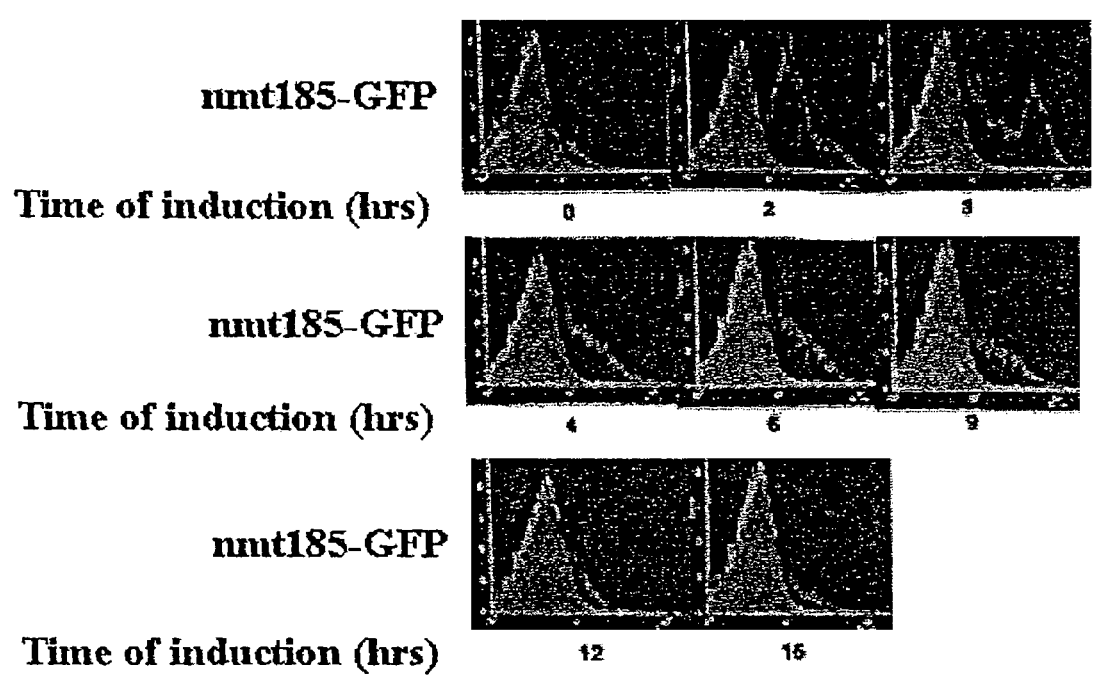

FIG. 6 GFP expression under the control of nmt-185 was monitored at cells level by FACS analysis Wild type strain of *S. pombe* harbouring the plasmid expressing GFP gene under the control of nmt-185 promoter was grown up to mid-log phase at 37° C. (promoter off) and then transferred to fresh medium and further grown at 25° C. to induce gfp exprssion. Samples were taken at 0, 2, 3, 4, 6, 9, 12 and 15 hours of induction and analyzed. 10,000 cells were analyzed for fluorescence intensity using a Becton Dickson FACsort flow cytometer. Excitation was at 488 nm and detection was through a 530-30 nm filter. Counts: number of cells showing a given fluorescence. FL1-H: Fluorescence filter 1. For comparison, the background autofluorescence of the wild type strain is superimposed on the same profile.

Figure 7:
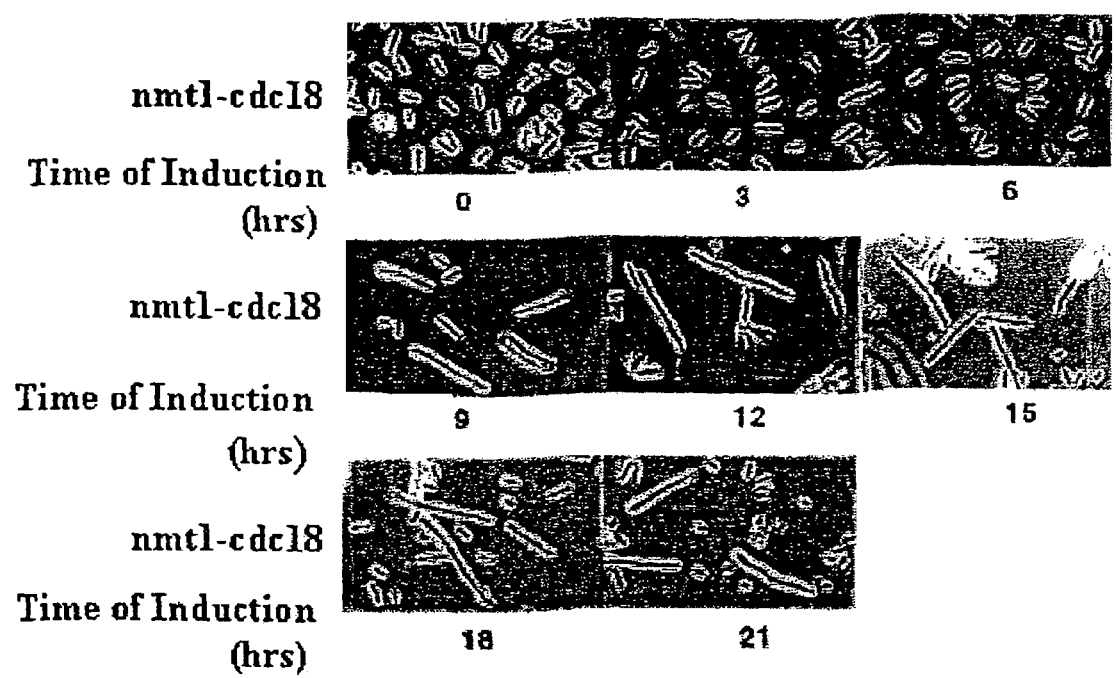

FIG. 7 The effect of overexpression of cec18 under the control of nmt1 promoter

Overexpression of cde18 leads to elongation of wild type cells. The wild type strain of *S. pombe* carrying cdc18 under the control of nmt1 were grown up to mid-log phase at 37° C. in presence of thiamine (repressed) and then transferred to fresh medium lacking thiamine and further grown at 25° C. (expressed). The samples were taken at times 0, 3, 6, 9, 12, 15, 18 and 21 hrs of induction and seen under the phase contrast microscope.

Figure 8:
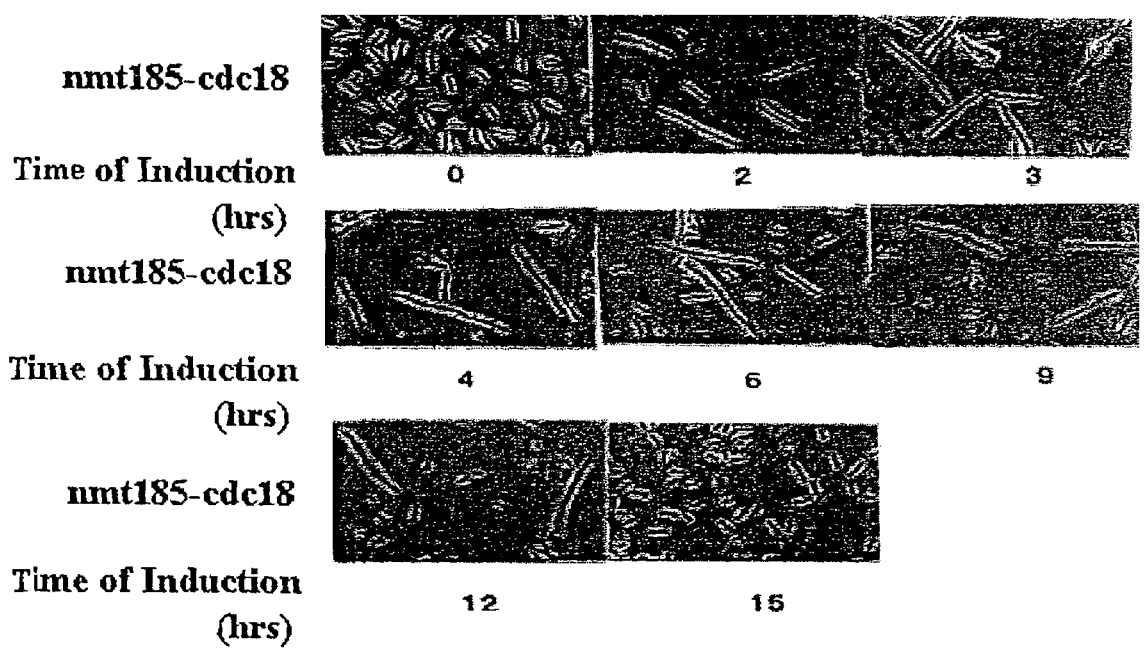

FIG. 8 The effect of overexpression of cec18 under the control of nmt-185 promoter Wild type strain of *S. pombe* expressing cec18 under the control of nmt-185 were grown up to mid-log phase at 37° C. (repressed) and then transferred to fresh medium and grown further at 25° C. (expressed). Samples were withdrawn after 0, 2, 3, 4, 6, 9, 12 and 15 hrs of induction and observed under the phase constrast microscope.

Figure 9:
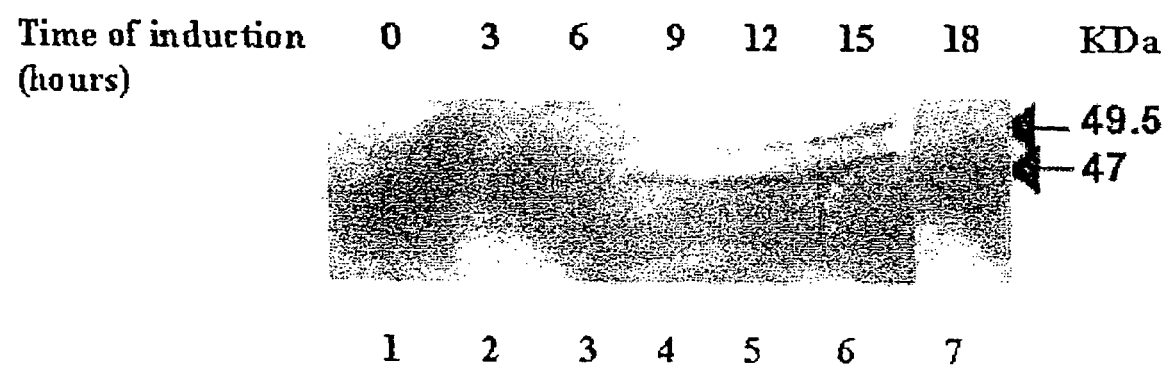

FIG. 9 The Kinetics of SK expression under the control of nmt1 promoter

Whole cell extracts were prepared from the cells harboring recombinant plasmid to pJRK1 (nmt1-SK, lanes 1-7) after 0, 3, 6, 9, 12, 15 and 18 hours of induction. The samples were subjected to SDS-PAGE (15%). Western blotted and probed with anti-SK polyclonal antibody. The unprocessed from (49 5 kDa) and mature form of SK (47 kDa) are indicated by bar line.

Figure 10:
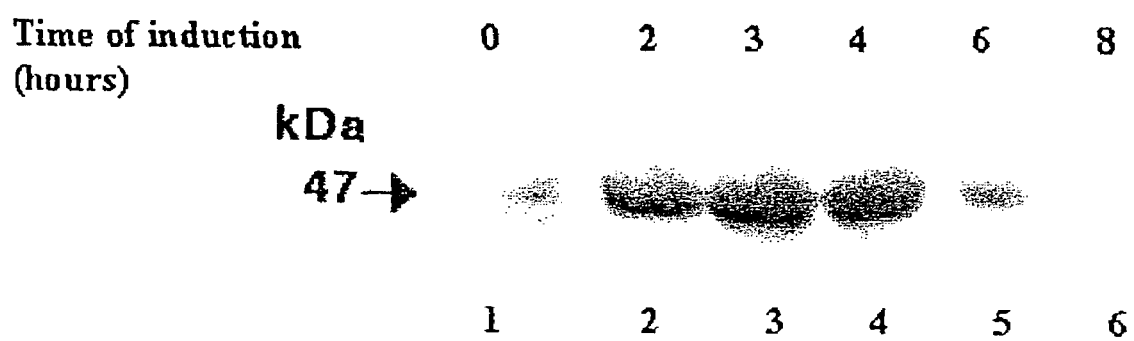

FIG. 10 The Kinetics of SK expression under the control of nmt-185 promoter

Whole cell extracts were prepared from the cells containing vector pJRK2 (lanes 1-6) after induction at 25° C. for different time points of induction. The samples were subjected to SDS PAGE (12.5%). Western blotted and probed with anti-SK polyclonal antibody. Mature SK (47 kDa) is indicated by arrows.

FIG. 11 Effect of expression of SK under the control of nmt1 (A) and nmt185 (B) promoters on the growth rate of the *S. pombe* wild type strains (A) Cells harboring vector (without promoter) or pJRK1 (nmt1-SK) were grown in PMA-leu medium containing thiamine for 18 hrs and further inoculated into fresh medium containing thiamine and grown up to $OD_{600}$=0.1. The culture was incubated for an additional 4-5 hrs at 30° C. to reach the mid-log phase. Thiamine was removed by washing and the cells were grown further in the medium lacking thiamine at the same temperature. Samples were withdrawn at the indicated time points up to 15 hrs. their $OD_{600}$ recorded and plotted.

(B) Cells harboring vector (without promoter) or nmt185-SK were grown in PMA-leu medium at 36° C. for 18 hrs and further inoculated in fresh medium up to $OD_{600}$=0.1. The culture was incubated for an additional 4-5 hrs at 36° C. to reach the mid-log phase. Cells were then shifted to 25° C. and grown further. Samples were withdrawn at the indicated time points up to 8 hrs, the $OD_{600}$ recorded and plotted FIG. 12 Fractionation of Sk expressed either with nmt1 or nmt-185 promoters (A & B) The periplasmic (PP) and cytoplasmic (CPP) fractions were prepared and subjected to SDS-PAGE (12.5%). Western blotted and probed with anti-SK polyclonal antibody lane 1, PP fraction, lane 2, CPP fraction, lane 3, pellet fraction of the wild type cells harboring plasmid pJRK1 (nmt1-SK) or pJRK2 (nmt185-SK). The band of 45 kD in the periplasmic fraction, which results from proteolysis, is indicated by arrow. Note that the level is much higher in case of nmt1-SK (about 50%) than in case of nmt185-SK (~5%).

SUMMARY OF THE INVENTION

The process of the present invention involves construction of a genomic library of *S. pombe* upstream of the GFP-reporter gene in a suitable vector that contains the ars1 element and the *S. cerevisiae* β-isopropylmalate dehydogenase (LEU2) or the *S. pombe* orotidinephosphate decarboxylase ura4 gene as a selectable marker, and plating this library on appropriate media containing different metal salts or monovalent salts as inducers or growth at different ambient temperatures. The expression of GFP was monitored by exposure to UV light and the putative clones expressing GFP were subjected to more careful screening. From an extensive search, two promoter elements were isolated that allowed expression of the GFP reporter gene at 25° C. but not at 36° C.

DETAILED DESCRIPTION OF THE INVENTION

The advantages of the new promoters vis-a-vis the nmt1 and its other known derivative promoters strongly support the aspects of novelty and lack of obviousness and anticipation. In fact, literature published on the characteristics of the nmt1 promoters have only focussed on the minimal size of the nmt1 promoters that is repressible by thiamin and on the role of trans-acting factors. No investigation has envisaged or anticipated in published literature whether derivatives of the nmt1 promoter having altogether new characteristics different from the original parent promoter could be derived. In fact, from our screen we were expecting to isolate heat-inducible promoters, like heat shock promoters, rather than the temperature sensitive ones that we actually obtained. Thus, identification of promoter that is heat sensitive, was an unexpected discovery for us as well. Therefore, we believe that these points will strengthen the claims for lack of obviousness and anticipation in obtaining the present set of promoters.

For construction of the genomic library, genomic DNA was isolated from wild type *S. pombe* strain having no known auxotrophic markers. Partial digestion of the genomic DNA was carried out with Sau3AI, to obtain maximum amount of DNA in the range of 100 bp to 2000 bp. The Sau3AI digested genomic DNA was ligated to the unique BamHI site in the vector pGFP (without nmt1 promoter) as per the standard procedure.

The above *S. pombe* 'promoter' library with GFP reporter was transformed into an *S. pombe* strain according to the published procedure of Gietz et al., 1992, *Nucleic acids Research* 20(6): 1425. The yeast transformants were replica plated on PMA-leu plates containing different concentration of glucose, galactose, sodium chloride, copper and zinc. The same transformants were also replica plated on to PMA-leu plate in triplicate and incubated at different temperatures. Expression was followed under the different conditions by directly monitoring the green fluorescence of colonies when exposed to UV.

Two clones were isolated from the above screen that exhibited enhanced expression of GFP at 25° C. and no expression at 36° C., as monitored by green fluorescence when exposed to the UV light.

Automatic DNA sequencer (PE Applied Biosystems ABI 310) was used for sequencing of these clones. The DNA samples were processed for sequencing according to ABI Prism BigDye Terminator protocol (PE Applied Biosystems). The clones yielded sequences of 185 and 146 bases and, therefore, the new promoters were named as nmt-185 (FIG. 1) and nmt-146 (FIG. 2), respectively.

A new vector pJRK2 (Accession no. MTCC 5106) was designed in which the nmt-185 promoter was cloned between the sites HindIII and PstI, followed by multiple cloning sites (MCS) including SalI, XhoI, BamHI, SmaI and SacI, into which other genes of interest could be cloned (FIG. 3).

Another new vector pJRK3 (Accession no. MTCC 5107) was designed in which the nmt-146 promoter was cloned between the sites HindIII and PstI, followed by multiple cloning sites (MCS) including SalI, XhoI, BamHI, SmaI and SacI, into which other genes of interest could be cloned (FIG. 4).

Because the new promoters show 100% homology with nmt1 gene of *S. pombe*, experiments were carried out to check whether conditions of repression and expression by the new promoters are similar to or different from those with nmt1 and to compare the strength as well as time of induction, using gfp-gene as a reporter gene. To compare the conditions of expression and repression of nmt-185, nmt-146 and nmt1 promoters, pGFP plasmids containing nmt-185, nmt-146 or nmt1 promoters were transformed into a wild type strain of *S.*

*pombe*. GFP expression was monitored in the presence and absence of thiamine at 36° C. and 25° C. It was observed that nmt1, nmt-146 and nmt-185 promoters were repressed in presence of thiamine at 36° C. as monitored by green fluorescence. However, in absence of thiamine at 36° C., while nmt1 promoter was derepressed, i.e., GFP gave green fluorescence, the nmt-185 and nmt-146 promoter remained repressed, i.e., GFP gene gave no green fluorescence. On the other hand at 25° C., nmt1, nmt-185 and nmt-146 were expressed as indicated by green fluorescence. When grown in absence of thiamine. But in presence of thiamine all three promoters were again repressed. Thus, the nmt-185 and nmt-146 promoters can be regulated by a temperature shift: they are repressed at 36° C., but expressed upon shift to 25° C. in absence of thiamine. In contrast, the nmt1 promoter is equally expressed at 36° C. and 25° C. in absence of thiamine.

A wild type strain of *S. pombe* carrying the clone for new promoters (nmt-185 and nmt-146) upstream of GFP gene was grown in YEA medium at 33-37° C. Overnight cultures were reinnoculated into YEA media and grown further at 33-37° C. to mid-log phase. They were washed thrice with sterile water, resuspended in PMA-leu media and grown further at 22-28° C. for 1-5-hrs. Cells were collected by centrifugation, washed in sterile water, and fixed by suspending in water, after which it was diluted with ethanol and stored at low temperature indefinitely. The fixed cells were harvested for analysis by centrifugation, washed with water and resuspended in 50 mM sodium acetate. Cells suspensions were sonicated briefly and analyzed using a FACSorting apparatus and data of fluorescence (FL1) plotted against forward scatter (FSC) or count against fluorescence (FL1).

Other genes, like β-galactosidase, Streptokinase from *S. equisimilis* and cdc18 from *S. pombe* were cloned in front of the new promoter element nmt-185 in the new vector pJRK2 (Accession no. MTCC 5106) (FIG. 3) and their expression was also monitored.

Other genes, like β-galactosidase, Streptokinase from *S. equisimilis* were also cloned in front of the new promoter element nmt-146 in the new vector pJRK3 (Accession no. MTCC 5107) (FIG. 4) and their expression was also monitored.

Assay for β-galactosidase activity was carried out as described by Davenport et al., 1999 *Genetics* 153: 1091-1103.

Samples were withdrawn from cells expressing the cdc18 gene under the control of the nmt-185 promoter at different time points of induction and examined under the Phase-contrast microscope.

Wild type cells harboring the Streptokinase gene under the control of nmt-185 or nmt-146 promoters were grown in YEA medium up to mid-log phase and then inoculated into synthetic PMA medium lacking uracil to start the induction of SK expression. Samples were collected after different times of induction. To obtain cell extracts the harvested cells were washed once with chilled water and then with Buffer A (0.02M Hepes, pH 7.5, 0.1M Sodium chloride, 0.002M EDTA, 0.625% glycerol and 1 mM β-mercaptoethanol). The cell pellet was resuspended in Buffer A containing protease inhibitors. An equal weight of acid-washed glass beads was added and cells broken by vortexing at 4° C. Each one min cycle of vortexing was followed by 30 sec incubation on ice till 80% lysis occurred. Cells lysate was centrifuged at 55,000 rpm for 1 hr at 4° C. in TL-100-3 rotor of TL-100 ultracentrifuge. The supernatant (cell extract) was saved and stored at −70° C. for further analysis.

Biologically active SK was quantitated as described by Jackson et al., 1981, Methods Enzymol. 80: 387-394.

Accordingly, the main embodiment of the present invention relates to novel temperature regulated promoters having SEQ ID No.1, designated as nmt-185 and SEQ ID No.2, designated as nmt-146.

Another embodiment of the present invention relates to the novel temperature regulated expression vectors having Accession No. MTCC 5106 and MTCC 5107 deposited at International depository of Institute of Microbial Technology (IMTECH), Chandigarh, India, wherein,
  (a) expression vector having Accession MTCC 5106 is harbouring temperature regulated promoter having SEQ ID No.1, designated as nmt-185 and
  (b) expression vector having Accession No. MTCC 5107 is harbouring temperature regulated promoter having SEQ ID No. 2, designated as nmt-146.

Yet another embodiment of the present invention relates to the a process of isolating novel temperature regulated promoters from *Scizosaccharomyces pombe* said process comprising the steps of:
  (a) constructing a partial genomic DNA library with restriction enzyme Sau3AI, to obtain partial genomic DNA sequences in the range of about 100 bp to 2000 bp,
  (b) ligating the genomic DNA library sequences of step (a) with vector pGFP without a promter
  (c) transforming the vector of step (b) to *S. pombe* strain,
  (d) screening of *S. pombe* strain containing the promoter library,
  (e) isolating and identifying two clones of (step d) by stimulating GFP expression,
  (f) using the clones obtained in step (e) to check repress or express of GFP expression by temperature shift,
  (g) sequencing the genomic DNA fragments of (f) as new promoter elements having SEQ ID No. 1 and SEQ ID No.2, designating the promoters as nmt-185 and nmt-146, useful as promoters,
  (h) cloning the said promoter elements into the novel vectors having Accession nos. MTCC 5106 and 5107 respectively.

Still another embodiment of the present invention relates to a process of preparing novel expression vectors based temperature regulated novel promoter elements isolated from *Scizosaccharomyces pombe* said process comprising steps of:
  (a) constructing a partial genomic DNA library with restriction enzyme Sau3AI, to obtain partial genomic DNA sequences in the range of about 100 bp to 2000 bp,
  (b) ligating the genomic DNA library sequences of step (a) with vector pGFP without a promter,
  (c) transforming the vector of step (b) to *S. pombe* strain,
  (d) screening of *S. pombe* strain containing the promoter library,
  (e) isolating and identifying two clones of (step d) by stimulating GFP expression,
  (f) using the clones obtained in step (e) to check repress or express of GFP expression by temperature shift,
  (g) sequencing the genomic DNA fragments of (f) as new promoter elements having 185 bases and 146 bases, named as nmt-185 and nmt-146 respectively, useful as promoters, and
  (h) cloning the said promoter elements into the novel vectors having Accession nos. MTCC 5106 and 5107 respectively.

One more embodiment of the present invention relates to a process wherein the step (f) the temperature shifts are 25° C. and 37° C.

Yet another embodiment of the present invention relates to the promoters wherein said promoters have been isolated from *Schizosacchromyces pombe*.

Another embodiment of the present invention relates to promoter wherein the sequence of the said promoter element nmt-185 and nmt-146 is identical or more than 80% homologous to the sequence of nmt1.

Still another embodiment of the present invention relates to promoter wherein the promoter element nmt-185 and nmt-146 are repressed in the temperature range of about 330 to 37° C.

Yet another embodiment of the present invention relates to a promoter wherein the promoter element nmt-185 and nmt-147 are expressed in the temperature range of about 220 to 28° C.

One more embodiment of the present invention relates to a promoter wherein the promoter element nmt-185 is about 185 bases long.

Another embodiment of the present invention relates to a promoter wherein the promoter element nmt-146 is only 146 bases long.

Yet another embodiment of the present invention relates to the promoter wherein the promoter elements nmt-186 and nmt-145 can express or repress the genes GFP, Streptokinase, β-galactosidase and cdc18 gene.

Still another embodiment of the present invention relates to promoters wherein the GFP expression of said promoters is about 95% within 3 hrs.

One more embodiment of the present invention relates to promoters wherein GFP expression of said promoters is about 91.4% within 3 hrs.

Another embodiment of the present invention relates to promoters wherein said promoters have β-galactosidase activity of about 150±20 units within 3 hrs of induction.

Still another embodiment of the present invention relates to promoters wherein said promoters have β-galactosidase activity of about 124.3±20 units within 3 hrs of induction.

Yet another embodiment of the present invention relates to promoters wherein said promoters have maximum specific activity of about 900 I.U/mg in 3 hrs.

One more embodiment of the present invention relates to promoters wherein said promoters have maximum specific activity of about 870±16 I.U/mg in 3 hrs.

Still another embodiment of the present invention relates to promoters wherein said promoters enhance expression of cdc-18 gene within 3 hrs of induction.

Another embodiment of the present invention relates to promoters wherein said promoters give lower leaky expression of proteins.

One more embodiment of the present invention relates to promoters wherein said promoters are not deleterious to the cell viability.

Yet another embodiment of the present invention relates to promoters wherein said promoters reduce the level of proteolytic degradation.

The process of the present invention is illustrated in the examples given below which should not, however, be construed to limit the scope of the present invention.

EXAMPLES

Example 1

Isolation of Promoter Elements

For search of promoters, a genomic library was constructed. For this, genomic DNA was isolated from wild type *S. pombe* strain having no known auxotrophic markers. Partial digestion of the genomic DNA was carried out with Sau3AI, to obtained maximum amount of DNA in the range of 100 bp to 2000 bp. The Sau3AI digested genomic DNA was ligated to the unique BamHI site in the vector pGFP (without promoter).

The above *S. pombe* 'promoter' library with GFP reporter was transformed into *S. pombe* strain. The yeast transformants were replica plated on PMA-leu plates containing different concentration of glucose, galactose, sodium chloride, copper and zinc. The same transformants were also replica plated on to PMA-leu plate in triplicate and incubated at different temperatures. Expression was followed under the different conditions by directly monitoring the green fluorescence of colonies when exposed to UV.

Two clones were isolated from the above screen that exhibited enhanced expression of GFP at 25° C. and no expression at 36° C., as monitored by green fluorescence when exposed to the UV light.

Automatic DNA sequencer (PE Applied Biosystems ABI 310) was used for sequencing of these clones. The DNA samples were processed for sequencing according to ABI Prism BigDye Terminator protocol (PE Appied Biosystems). The clones yielded sequences of 185 and 146 bases and, therefore, the new promoters were named as nmt-185 (FIG. 1) and nmt-146 (FIG. 1), respectively.

A new vector (Accession no. MTCC 5106) was designed in which the nmt-185 promoter was cloned between the sites HindIII and PstI, followed by multiple cloning sites (MCS) including SalI, XhoI, BamHI, SmaI and SacI, into which other genes of interest could be cloned (FIG. 2).

Another new vector (Accession no. MTCC 5107) was designed in which the nmt-146 promoter was cloned between the sites HindIII and PstI, followed by multiple cloning sites (MCS) including SalI, XhoI, BamHI, SmaI and SacI, into which other genes of interest could be cloned (FIG. 3).

Both these vectors were deposited in International Depository Authority on Microbial Type Culture Collection and have given accession nos. MTCC 5106 and 5107 respectively.

Example 2

Expression of GFP by nmt-185 Promoter

To monitor the expression level induced by the new promoter element, the gene encoding the green fluorescent protein (GFP) was cloned in the MCS of the vector pJRK2 (Accession no. MTCC 5106) (FIG. 3). The same gene was also cloned in front of the nmt1 promoter for comparison of level of expression. Flow cytometry analysis was used to quantify the amount of GFP protein expressed under the control of nmt-185 at different time intervals of induction. As yeast cells have some background autofluorescence when irradiated at 488 nm, the fluorescence profile of *S. pombe* strain having control vector was analyzed first. *S. pombe* cells were grown to mid-exponential phase in rich medium under repressed conditions (36° C.) and then shifted to expressed condition in a selective medium (25° C.). Samples were taken at 0, 2, 3, 4, 6, 9, 12, and 15 hours of induction and the fluorescence profile of 10,000 cells analyzed. In case of the nmt-185 promoter, the fluorescence signal was maximum after a 3 hr period of induction, followed by a decrease with further increase in time of induction.

The study of the present shows that nmt-185 promoter also gives maximum GFP expression after 3 hours of induction, while nmt1 promoter does so only after 15 hours of induction. Furthermore, the level of expression appears to be similar in both cases as indicated by similar fraction of cells expressing GFP by both the promoters (FIGS. 4 to 6; Table 1).

TABLE 1

Levels of GFP expression under the control of nmt-185 and nmt1 promoters. Samples drawn at different time points of induction were analyzed by FACS.*

| | | GFP expression level (nmt-185 promoter) | | GFP expression level (nmt1 promoter) | |
|---|---|---|---|---|---|
| Sr. No. | Time (Hrs) | % non-expressing cells | % Expressing cells | % non-expressing cells | % expressing cells |
| 1 | Control | 98.55 | 1.45 | 99.01 | 1.01 |
| 2 | 0 | 97.84 | 2.16 | 98.98 | 1.04 |
| 3 | 2 | 63.03 | 36.97 | — | — |
| 4 | 3 | 8.60 | 91.4 | 98.26 | 1.74 |
| 5 | 4 | 72.57 | 27.43 | — | — |
| 6 | 6 | 71.86 | 28.14 | 94.42 | 5.86 |
| 7 | 9 | 77.81 | 22.19 | 89.54 | 10.46 |
| 8 | 12 | 89.40 | 10.60 | 29.74 | 71.26 |
| 9 | 15 | 95.12 | 4.88 | 4.72 | 95.28 |
| 10 | 18 | — | — | 53.21 | 47.34 |
| 11 | 21 | — | — | 58.83 | 42.17 |

*This was calculated by using Kolmogarov-Smirnov Statistics Programme.
— denotes for not determined.

Example 3

Expression of cdc18 Gene of *S. pombe* by nmt-185 Promoter

The new promoter element nmt-185 isolated from the promoter screen was also used to monitor the expression of cell division cycle gene cdc18 from *S. pombe*. Overproduction of cdc18 has been shown to cause delay in mitosis and more than one round of DNA synthesis leading to a drastic elongation of cells. In the present example expression of cdc18+gene was carried out under the control of nmt-185 promoter.

The cdc18 gene was cloned into the multiple cloning sequence (MCS) of the vector pJRK2 (Accession no. MTCC 5106) and transformed in to a wild type strain of *S. pombe*. Similarly, the cdc18 gene was also cloned in front of the nmt1 promoter. Cells were grown to exponential phase in medium containing thiamine (promoter off) at 36° C., washed extensively and transferred to fresh media without thiamine at 25° C. (promoter on) to induce the expression of cdc18. Samples were withdrawn after 0, 2, 3, 4, 6, 9, 12, and 15 hours of induction and examined under the Phase-contrast microscope. In case of nmt-185 promoter, cells start becoming elongated after 2 hrs of induction and achieved maximum elongation after 3 hrs. Further, see the data for expression of cdc 18 by nmt1 and nmt-185 promoters in and FIGS. 7 and 8, respectively. These data also indicate that maximum effect of overexpression of cdc18, visualized as fraction of elongated cells, is achieved by 3 hours with nmt-185 promoter (FIG. 7), while it takes 15-18 hours when expressed under the control of nmt1 promoter (FIG. 7).

Example 4

Expression of β-Galactosidase by the nmt-185 Promoter

The PstI-XhoI fragment containing the nmt-185 promoter was cloned into the PstI and XhoI sites of the vector pREP3X-lacZ in place of the nmt1 promoter (Maundrell, 1990, J. Biol. Chem. 265: 10857-10864). Thus, the lacZ gene was expressed under control of nmt-185 promoter and the β-galactosidase activity monitored at 0, 2, 3, 4, 6, 9, 12 and 15 hours of induction using ONPG as substrate. Activity was maximum after 3 hrs of induction in case of nmt-185 promoter. The nmt-185 promoter induced β-galactosidase by approximately 25-fold. See comparison of expression of (5-galactosidase by pREPS, pREP41, pREP81 and pREP-185 in Tables 2 and 3. The data show that pREP-185 promoter allows expression at the same level as that shown by the promoter pREP41, i.e., moderate level of expression. Furthermore, it shows a similarly low level of leaky expression as pREP41 under repressed condition. However, the nmt-185 promoter is better than even nmt1, which is the strongest version of nmt promoter, in that it shows maximum expression after only 3 hours of induction (Table 3), while nmt1 gives maximum expression only after 15 hours of induction.

TABLE 2

Comparison of β-galactosidase activity of known promoters of *S. pombe* with nmt-185 promoter

| Vector | Promoter | Repressed conditions In Units | Induced conditions In Units | Approx. Induction Ratio | Ref. |
|---|---|---|---|---|---|
| pREP3X-lacZ | nmt1 (full strength) | 24.7 ± 9 | 7395 ± 404 | 300X | Forsburg, 1993. |
| pREP41X-lacZ | nmt1 (weaker) | 5.1 ± 1 | 121 ± 3 | 25X | |
| pREP81X-lacZ | nmt1 (weakest) | 1.2 ± 0.3 | 7.2 ± 2 | 7X | |
| pREP3X-lacZ | nmt1 (full strength) | 7.59 ± 1.3 | 2053 ± 65 | 271X | Present Invention |
| pREP/185-lacZ* | nmt-185 | 5.4 ± 1.0 | 124.3 ± 20 | 25X | Present Invention |

*nmt1 promoter fragment of vector pREP3X-lacZ was replaced with the nmt-185 promoter fragment.

TABLE 3

Levels of β-galactosidase activity expressed at different times of induction of lacZ gene when expressed under the control of nmt1 and nmt-185 promoters.

| Sr. No. | Induction time (Hrs) | β-gal activity (nmt-185 promoter) (Units) | β-gal activity (nmt1 promoter) (Units) |
|---|---|---|---|
| 1. | 0 | 5.4 ± 1.0 | 7.59 ± 1.3 |
| 2. | 2 | 56.8 ± 12 | — |
| 3. | 3 | 124.3 ± 20 | 8.65 ± 1.2 |
| 4. | 4 | 29.0 ± 12 | — |
| 5. | 6 | 16.25 ± 6.2 | 42.65 ± 11.8 |
| 6. | 9 | 13.82 ± 5.2 | 130.02 ± 12.6 |
| 7. | 12 | 13.67 ± 6.4 | 1845.2 ± 45 |
| 8. | 15 | 10.23 ± 3.4 | 2053 ± 65 |
| 9. | 18 | — | 1025 ± 42 |
| 10. | 21 | — | 825 ± 20 |

— denoted for not determined.

Example 5

Expression of Streptokinase by the nmt-185 Promoter

To check whether a heterologous gene can be expressed by the new promoter, a chimeric gene construct comprising a fusion between the Plus pheromone signal sequence of *S. pombe* and the mature SK was cloned in front of the nmt-185 promoter in the vector pJRK2 (Accession no. MTCC 5106).

The cloned plasmid was transformed into a wild type strain of S. pombe and the transformants were selected for uracil prototrophy at 37° C. To assess the level of SK activity, plasminogen clearing plate assay was performed by replica plating, overlaying with skim milk-agarose containing plasminogen and incubating at 25° C. After 4 hrs, the transformants harboring the plasmid expressing SK gene produced a clear zone. Thus, the recombinant plasmid harboring the Streptokinase gene under the control of nmt-185 promoter also expresses SK activity in S. pombe.

To obtain the optimum conditions for expression using the new promoter, wild type cells expressing the recombinant plasmid pJRK2 (accession no. MTCC 5106) containing the chimeric Plus- factor-SK fusion gene were grown in YEA medium at 37° C. up to mid-log phase and then inoculated into synthetic PMA medium lacking uracil at 25° C. to start the induction of SK expression. Samples were collected after 2, 3, 4, 6 and 8 hrs of induction. At the same time points culture supernatants were also collected and concentrated. No SK activity was observed in supernatant. Cell extracts were subjected to SDS-polyacrylamide gel electrophoresis, followed by immunoblotting with anti-SK antibody. One band of 47 kDa corresponding to mature SK could be observed. SK activity in the extract was quantitated using chromozyme substrate and maximum level of specific activity of 870 I.U./mg protein was observed after 3 hrs of induction. The activity decreased significantly after 4 hrs of induction and no activity could be detected after 6 and 8 hrs of induction. No activity could be detected in the culture supernatant at any time point. The data for expression of streptokinase by nmt1 in FIG. 9 and that by nmt-185 promoter in FIG. 10 and the comparison of the maximum activities using the two promoters and the time of induction in Table 4. These data again show that nmt-185 promoter yields maximum expression of SK within 3 hours of induction, as compared with 15 hours required by the nmt1 promoter (Table 5).

Although nmt1 remains expressed over a wide temperature range, its benefit is counterbalanced because of the long induction period, toxicity, metabolic load and cumbersome handling required to remove the represser (thiamin) by repeated washings. On the other hand in case of the new promoters, the induction step involving reducing the temperature from 36° C. to 25° C. is operationally easy to perform, without a change of medium. Along with other advantages, like reduced induction period (from 15 hrs with nmt1 to 3 hours with nmt185/nmt146), no effect on growth rate and reduced level of toxicity and proteolysis, possibly because of the reduced time of exposure of the expressed protein, makes the new promoters much more advantageous to use (This has been discussed as below).

The inventors have performed experiments to compare the growth rates of cultures expressing Streptokinase (SK) under the control of nmt1 and nmt185 promoters and find that while in the case of nmt1-induced expression there is 50% reduction in growth rate accompanying the induction of SK expression (compare FIG. 11 with FIG. 9), there is no effect on growth when SK was expressed under the control of nmt185 (Compare FIG. 11 with FIG. 10). The FIG. 11 is suggesting lack of toxicity and/or reduction of growth rate while using nmt-185 promoter in contrast with nmt1 promoter.

Figure 12:
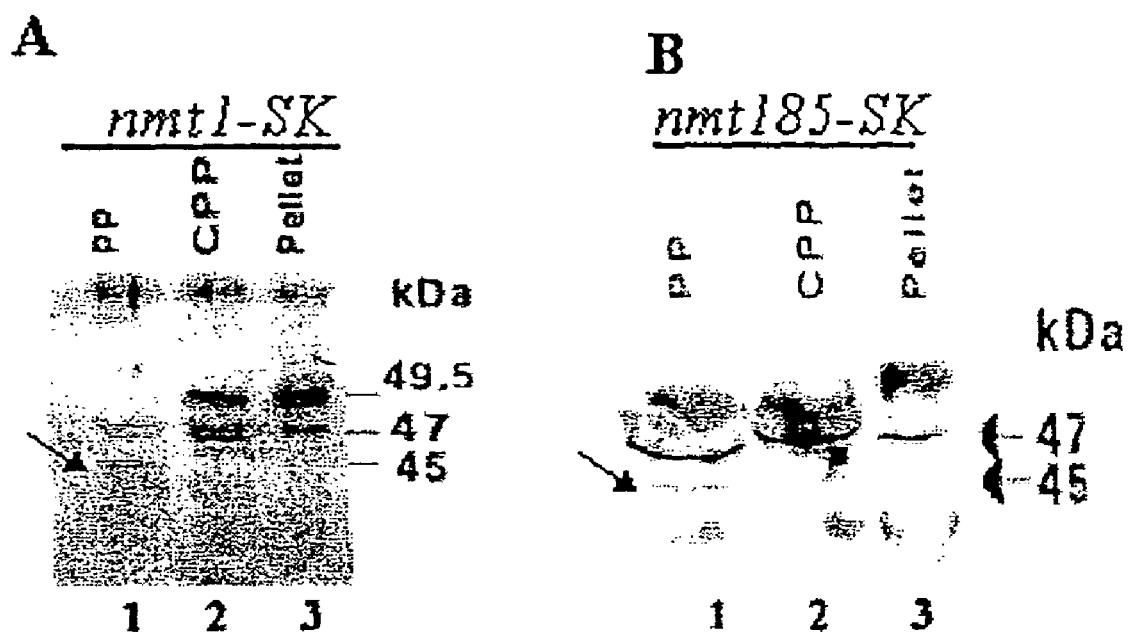

Likewise, while significant level of proteolysis of SK is observed in the periplasmic fraction of cells expressing SK under the control of nmt1 promoter, less than 5% proteolysis of SK was observed in the periplasmic fraction of cells expressing SK under the control of nmt185 promoter. Thus, expression with the nmt-185 promoter results in very much reduced proteolysis in the periplasmic fraction as compared to expression by the nmt1 promoter, which may be due to reduced time of exposure of protein to the extracellular or periplasmic proteases. This data is shown in FIG. 12.

TABLE 4

Comparison of maximum Specific activity of SK achieved when expressed Under he control of nmt1 and nmt185 promoters

| Time | Specific activity (I.U./mg) | |
|---|---|---|
| (Hrs) | nmt1 | nmt 185 |
| 3 | — | 870 ± 16 |
| 15 | 1581 ± 80 | — |

— denotes no detectable SK activity.

TABLE 5

Comparison of Expression levels of different genes under the control of nmt1 and nmt-185 promoter.

| | | nmt-185 promoter | | nmt1 promoter | |
|---|---|---|---|---|---|
| Sr. No. | Gene Expressed | Time of Induction (hrs) | Level of expression (max.) | Time of Induction (hrs) | Level of expression (max.) |
| 1. | gfp | 3 | 91.4%@ | 15 | 95.28%@ |
| 2. | SK | 3 | 870 IU/mg | 15 | 1581 IU/mg |
| 3. | β-gal | 3 | 124 U | 15 | 2053 U |
| 4. | cdc18 | 3 | max. elongated cells | 15 | max. elongated cells |

@% age of cells expressing gfp.
U - units
I.U. - International units

Example 6

Expression of β-Galactosidase by the nmt-146 Promoter

The PstI-XhoI fragment containing the nmt-146 promoter was cloned into the PstI and XhoI sites of the vector (pREP3X-lacZ) in place of the nmt1 promoter (Maundrell, 1990, J. Biol. Chem. 265: 10857-10864). Thus, the lacZ gene was expressed under control of nmt-146 promoter and the β-galactosidase activity monitored at 0, 2, 3, 4, 6, 9, 12 and 15 hours of induction using ONPG as substrate. Activity was maximum after 3 hrs of induction in case of nmt-146 promoter. Like nmt-185, the nmt-146 promoter also induced β-galactosidase by approximately 25-fold.

Example 7

Expression of Streptokinase by the nmt-146 Promoter

To check whether a heterologous gene can be expressed by the new promoter, a chimeric gene construct comprising a fusion between the Plus pheromone signal sequence of S. pombe and the mature SK was cloned in front of the nmt-146 promoter in the vector pJRK3 (Accession no. MTCC 5107) (FIG. 4). The cloned plasmid was transformed into a wild type strain of S. pombe and the transformants were selected for uracil prototrophy at 37° C. To assess the level of SK activity, plasminogen clearing plate assay was performed by replica plating, overlaying with skim milk-agarose containing plasminogen and incubating at 25° C. After 4 hrs, the transformants harboring the plasmid expressing SK gene produced a clear zone. Thus, the recombinant plasmid harboring the Streptokinase gene under the control of nmt-146 promoter also expresses SK activity in *S. pombe* at levels similar to those obtained with the nmt-185 promoter.

The Advantages of the New Promoters nmt-185 and nmt1-46

Faster induction kinetics of the nmt-185 and nmt-146 promoters as compared to the nmt1 promoter: The nmt1 promoter provides maximum expression level after 18-20 hours of induction, while the nmt-185 and nmt-146 do so within 3 hours of induction-thus providing a 5-6 fold faster rate of induction than the nmt1 promoter.

This minimizes the problem of metabolic load. The faster kinetics of induction in case of the nmt-185 and nmt-146 promoters has another advantage that maximum level of expression of protein is achieved within less than one generation (5 hours), obivating the posulated of exerting a metabolic load on the host cells.

Low level of leaky expression of the protein: We find that the nmt-185 and nmt-146 promoters give much lower leaky expression levels as compared to the nmt1 promoter but similar to that observed with the nmt41, a moderately active derivative of the nmt1 promoter. This aspect provides for tighter control of expression.

Ease and reduced cost of manipulation: Operationally, the temperature shift from 36° C. (repressed) to 25° C. (expressed) is easy to perform and convenient for bench scale experiments and commercial process, as it significantly reduces the cost and time factor. In contrast, manipulations with the nmt1 promoter involve extensive washings to remove the repressor (thiamine) and suspending the cells in thiamin-free medium; these operations add to the cost of expression and production.

Minimum deleterious effect on cell viability The short time of induction, which is less than one generation time of the growing cells, minimizes the cells' exposure to the toxic effects of the protein.

Reduced level of proteolytic degradation. The reduced time of exposure of the expressed protein to the cellular environment before being harvested also results in reduced level of degradation by the intracellular proteases.

We claim:

1. An isolated promoter for inducible expression of homologous and heterologous proteins, wherein said promoter consists of SEQ ID NO: 1 or SEQ ID NO: 2, and wherein said promoter is induced by a reduction in temperature.

2. An expression vector comprising the promoter of claim 1, wherein said promoter is linked to a DNA encoding GFP and wherein said GFP is maximally expressed in *S. pombe* cells within three hours of when the *S. pombe* cells are subjected to a temperature shift from 36° C. to 25° C.

3. The promoter of claim 1 wherein said promoter is linked to a DNA encoding β-galactosidase, and wherein said β-galactosidase is maximally expressed in *S. pombe* cells within three hours of when the *S. pombe* cells are subjected to a temperature shift from 36° C. to 25° C.

4. The promoter of claim 1 wherein said promoter is linked to a DNA encoding cdc 18, and wherein said cdc 18 is maximally expressed in *S. pombe* cells within three hours of when the *S. pombe* cells are subjected to a temperature shift from 36° C. to 25° C.

5. The promoter of claim 1 wherein said promoter is linked to a DNA encoding streptokinase, and wherein said streptokinase is maximally expressed in *S. pombe* cells within three hours of when the *S. pombe* cells are subjected to a temperature shift from 36° C. to 25° C.

6. A vector comprising an isolated promoter for the inducible expression of homologous and heterologous proteins, wherein said vector is selected from the group consisting of a vector deposited under Accession No. MTCC 5106 and a vector deposited under Accession No. MTCC 5107.

7. The vector of claim 6, wherein said vector further comprises an open reading frame encoding GFP.

8. The vector of claim 6, wherein said vector further comprises an open reading frame encoding β-galactosidase.

9. The vector of claim 6, wherein said vector further comprises an open reading frame encoding cdc-18.

10. The vector of claim 6, wherein said vector contains an open reading frame encoding streptokinase.

11. A method for inducing the synthesis of a homologous protein or a heterologous protein, comprising incubating a *S. pombe* cell transformed with a DNA comprising the promoter of claim 1 operably linked to a gene encoding said homologous protein or said heterologous protein at 25° C. for about 3 hours.

12. A method for inducing the synthesis of a homologous protein or a heterologous protein, comprising incubating a *S. pombe* cell transformed with the vector of claim 6 wherein the vector further comprises a gene encoding said homologous protein or said heterologous protein at 25° C. for about 3 hours.

* * * * *